United States Patent [19]

Ichitsuka et al.

[11] Patent Number: 5,089,195

[45] Date of Patent: * Feb. 18, 1992

[54] METHOD FOR PRODUCING CALCIUM PHOSPHATE-BASED MATERIAL

[75] Inventors: Takeshi Ichitsuka; Yasuhiko Hirayama; Tetsuro Ogawa, all of Tokyo, Japan

[73] Assignee: Asahi Kogaku Kogyo K.K., Tokyo, Japan

[*] Notice: The portion of the term of this patent subsequent to Sep. 18, 2007 has been disclaimed.

[21] Appl. No.: 542,150

[22] Filed: Jun. 22, 1990

Related U.S. Application Data

[63] Continuation of Ser. No. 192,552, May 11, 1988, Pat. No. 4,957,674.

[30] Foreign Application Priority Data

May 12, 1987 [JP] Japan .............................. 62-115180

[51] Int. Cl.$^5$ ............................................. C04B 35/64
[52] U.S. Cl. ............................................. 264/65; 264/66; 501/123
[58] Field of Search ............... 264/65, 66, 64; 501/1, 501/123

[56] References Cited

U.S. PATENT DOCUMENTS

| | | | |
|---|---|---|---|
| 3,111,397 | 11/1963 | Metz | 264/64 |
| 3,922,155 | 11/1975 | Broemer | 65/33 |
| 4,097,935 | 7/1978 | Jarcho | 501/1 |
| 4,149,893 | 4/1979 | Aoki et al. | 501/123 |
| 4,767,583 | 8/1988 | Van der Meer | 264/66 |

FOREIGN PATENT DOCUMENTS

| | | |
|---|---|---|
| 0207561 | 1/1987 | European Pat. Off. |
| 1548066 | 7/1979 | United Kingdom |
| 1522182 | 8/1979 | United Kingdom |
| 1550330 | 8/1979 | United Kingdom |

*Primary Examiner*—James Derrington
*Attorney, Agent, or Firm*—Sughrue, Mion, Zinn, Macpeak & Seas

[57] ABSTRACT

A method for producing a calcium phosphate-based material comprising:
  (a) molding a calcium phosphate powder;
  (b) preliminarily calcining the resulting molding in a vacuum or under a reduced pressure until the relative density is 95% or more; and
  (c) firing the molding in air, an inert gas, or nitrogen gas.

8 Claims, No Drawings

METHOD FOR PRODUCING CALCIUM PHOSPHATE-BASED MATERIAL

This is a continuation of application Ser. No. 07/192,552 filed May 11, 1988, now U.S. Pat. No. 4,957,674.

FIELD OF THE INVENTION

The present invention relates to a method for producing a calcium phosphate-based material which is suitable, for example, for a bone-supplying material used in dental surgery, orthodepic surgery, otorhinolaryngology and the like.

BACKGROUND OF THE INVENTION

Recently, in dental surgery, orthodepic surgery, otorhinolaryngology and the like, artificial bone-supplying materials have been used to supply a lost part of bone due to the fracture of bone, a bone tumor, and pyorrhea alveolaris. Of these artificial bone-supplying materials, a calcium phosphate-based material exemplified by hydroxyapatite has received the greatest attention as an excellent bone-supplying material because of its high affinity to a living body. In addition to having good affinity to a living body, an artificial bone-supplying material is required to have a sufficiently high strength.

The calcium phosphate-based material used in the applications described above has heretofore been produced by press molding a calcium phosphate powder by techniques such as hot pressing (HP) and hot isostatic pressing (HIP) while at the same time heating, or press molding it by techniques such as cold isostatic pressing (CIP), and then firing the resulting molding at a temperature of about 1,000° C. In the calcium phosphate-based material thus obtained, as the relative density (where the density calculated with the density of a calcium phosphate-based material not containing any air bubbles is 100%) is higher, the strength generally tends to be higher.

In the method comprising heating simultaneously with press molding by techniques such as hot pressing (HP) and hot isostatic pressing (HIP), the strength can be increased by increasing the relative density. This method, however, has a problem in that large-scaled equipment is needed, leading to a marked increase in the production cost.

In the method comprising press molding by techniques such as cold isostatic pressing (CIP) and then firing, the relative density can be increased to a certain extent by increasing the firing temperature. In this method, however, a problem arises in that the calcium phosphate-based material starts to decompose at a firing temperature exceeding about 1,400° C., because the melting point of e.g., hydroxyapatite is about 1,650° C. For this reason, increasing the firing temperature is limited, and thus the ability to increase the relative density by raising the firing temperature is also limited.

Moreover, although the relative density can also be increased to a certain extent by raising the firing temperature, if the firing temperature is raised, the primary particles of the sintered body tend to become large. Thus, a problem arises in that the strength is not increased in proportion to an increase in the relative density.

SUMMARY OF THE INVENTION

An object of the present invention is to provide a method for producing a calcium phosphate-based material whereby a high relative density can be obtained at a relatively low firing temperature and thus the resulting material has an increased strength.

Other objects of the present invention will be apparent from the following description.

The above objects of the present invention have been met by a method for producing a calcium phosphate-based material comprising:

(a) molding a calcium phosphate powder;
(b) preliminarily calcining the resulting molding in a vacuum or under a reduced pressure until the relative density reaches at least 95%; and
(c) firing the molding in air, an inert gas, or nitrogen gas.

DETAILED DESCRIPTION OF THE INVENTION

In accordance with the method of the present invention, preliminary calcination is carried out in a vacuum or under a reduced pressure, and then the final firing is carried out. As a result, a high relative density can be obtained at a relatively low calcination temperature. Thus, a sintered body comprising fine primary particles and having a high relative density can be obtained so that its strength can be increased.

The present invention will hereinafter be explained in more detail below.

The calcium phosphate-based powder used as the starting material is not critical to the present invention. At least one of $Ca_{10}(PO_4)_6(OH)_2$, $Ca_3(PO_4)_2$, $Ca_2P_2O_7$, $Ca(PO_3)_2$, $Ca_{10}(PO_4)_6F_2$, and $Ca_{10}(PO_4)_6Cl_2$ are preferably used. Of these compounds, $Ca_{10}(PO_4)_6(OH)_2$ (hydroxyapatite) is particularly preferred. The above calcium phosphate-based compounds can be produced by various known methods such as the wet method in which a water-soluble phosphate and a water-soluble calcium salt are reacted in an aqueous solution, and the dry method in which a phosphoric acid compound and a calcium compound are reacted at elevated temperatures. The wet method is described, e.g., in Wallaeys, R.,. *Ann. Chim. (Paris)*, vol. 7, 808 and 823 (1952); Moreno, E. C., Gregory, T. M., Brown, W. E., *J. Res. Nat. Bur. Stand.*, vol. 72A, 773 (1968); and L. C. Bell, H. Mika, B. J. Kruger, *Archs. Oral. Biol.*, vol. 23, 329 to 336 (1978). The dry method is described, e.g., in Quinaux, N., *Arch. Intern. Physiol. Biochim.*, vol. 72, 337 (1964) and *Chem. Abstr.*, vol. 60, 15418a (1964); and Liteanu, C., Macarouci, D., *Studii Cercetari Chim.*, vol. 13, 157 (1962).

The calcium phosphate-based compound thus produced can be used as the starting material as it is. If necessary, however, it may be dried by techniques such as spray drying, provisionally calcined at a temperature of about 700° C., and then powdered.

In accordance with the present invention, the above calcium phosphate-based powder is press molded into the desired shape. The molding method is not critical to the present invention. A method which is preferably employed comprises applying primary molding using, for example, a metal mold and then applying secondary molding using, for example, a cold isostatic press (CIP).

Then, the resulting molding is subjected to preliminary calcination in a vacuum or under a reduced pressure until the relative density becomes 95% or more. It is important in this preliminary calcination that when closed pores are formed during the process that the body is made more dense, air (particularly nitrogen) is removed from the closed pores. If nitrogen remains in the pores, the pores disappear only with difficulty because the diffusion rate of nitrogen is small. Thus, until closed pores are formed, i.e., until the relative density is about 95%, preliminary calcination is carried out in a vacuum or under a reduced pressure, whereby air can be removed from the air pores and the density can be increased. The effect of the preliminary calcination cannot be obtained sufficiently if the relative density is less than 95%. In connection with the vacuum or a reduced pressure, it is preferred to adjust the pressure to less than 1 Torr. At a pressure of 1 Torr or more, air cannot be efficiently removed during the preliminary calcination step.

The temperature of the preliminary calcination is preferably from 950° to 1,100° C. If the temperature is less than 950° C., air cannot be removed effectively. On the other hand, if it is more than 1,100° C., there is the danger that the calcium phosphate-based compound will begin to decompose. The preliminary calcination is preferably carried out for about from 0.5 to 5 hours.

After the above preliminary calcination, the final firing is carried out in air, an inert gas, or nitrogen gas. As the inert gas, argon gas, helium gas and the like can be used. The temperature of the final firing is preferably from 1,000° to 1,400° C. If the temperature is less than 1,000° C., a sintered body of high density cannot be obtained. On the other hand, if it is more than 1,400° C, there is the danger that the calcium phosphate-based compound will begin to decompose. The final firing is preferably carried out for about from 0.5 to 5 hours.

In the present invention, a binder may be added to the calcium phosphate powder as the starting material. The binder is an organic combustible (heat-decomposable) material which is suitable for a powder molding assistant. Examples thereof include a polyvinyl alcohol, a carboxyl methyl cellurose, gum arabic, a polyvinyl butyral, an acryl emulsion, and the like.

The method according to the present invention may further comprises additional steps, such as a machining step using a lathe, etc. which is conducted after the primary molding or after the secondary molding; a decarbonizing step which is conducted before the preliminary calcination to bur up the binder; a finalizing step after firing which involves processing with a diamond grinder or the like to improve the dimensional accuracy or polishing to planish the surface; and the like.

The method of the present invention has the following advantages compared with the conventional methods. If the firing temperature is the same as that in the conventional methods, a sintered body having a higher density can be obtained. If a sintered body having the same density as that in the conventional methods is intended to be produced, the firing temperature can be decreased more. Thus, in accordance with the method of the present invention, the relative density of the sintered body can be increased while maintaining the firing temperature at a low level so that an increase in the size of the primary particles in the sintered body is prevented. Therefore, a calcium phosphate-based material having a high strength can be produced.

The calcium phosphate-based material thus produced is suitable as a bone-supplying material to be used in dental surgery, orthodepic surgery, otorhinolaryngology and the like.

The present invention is described in greater detail with reference to the following examples which are in no way intended to limit the present invention.

EXAMPLE 1

Hydroxyapatite was produced from calcium hydroxide ($Ca(OH)_2$) and phosphoric acid ($H_3PO_4$) as starting materials by the wet method. The slurry thus obtained was dried using a spray drier, provisionally calcined at 700° C. and then pulverized to obtain a hydroxyapatite powder.

This hydroxyapatite powder was subjected to primary molding using a metal mold and then subjected to secondary molding using a 2,000 kg/cm$^2$ cold isostatic press to obtain a pressed powder molding. The relative density of the pressed powder molding was about 52%.

This pressed powder molding was subjected to preliminary calcination under a reduced pressure of from $10^{-5}$ to $10^{-6}$ Torr at 960° C. for 2 hours.

Then, the molding was subjected to final firing in air at 1,050° C. for 4 hours. The hydroxyapatite sintered body thus obtained had a relative density of 99.5%.

For comparison, the same hydroxyapatite powder as above was pressed in the same manner as above to produce a pressed powder molding and then such was fired in air at 1,050° C. for 4 hours without application of preliminary calcination. The hydroxyapatite sintered body thus obtained had a relative density of 99.2%.

EXAMPLE 2

In the same manner as in Example 1, a hydroxyapatite powder was pressed to produce a pressed powder molding and further in the same manner as in Example 1, the pressed powder molding was subjected to preliminary calcination and then to final firing in air at 1,200° C. for 4 hours. The relative density of the hydroxyapatite sintered body thus obtained reached 99.8% This sintered body showed light transmission properties (hydroxyapatite shows light transmission properties when it has a high density).

For comparison, in the same manner as in Example 1, the hydroxyapatite powder was pressed to produce a pressed powder molding, and this pressed powder molding was calcined in air at 1,200° C. for 4 hours. The relative density of the hydroxyapatite sintered body thus obtained was 99.4%.

In accordance with the present invention, as described above, preliminary calcination is carried out in a vacuum or under a reduced pressure and, thereafter, final firing is carried out in air, an inert gas, or nitrogen gas. Therefore, the relative density of the sintered body thus obtained can be increased while maintaining the firing temperature at a low level so that an increase in the size of the primary particles of the sintered body can be prevented. Therefore a calcium phosphate-based material having a high strength can be produced. The calcium phosphate-based material thus obtained is suitable, e.g., as bone-supplying material to be used in dental surgery, orthodepic surgery, otorhinolaryngology and the like.

While the invention has been described in detail and with reference to specific examples thereof it will be apparent to one skilled in the art that various changes and modifications can be made therein without departing from the spirit and scope thereof.

What is claimed is:

1. A method for producing a calcium phosphate-based material comprising:
   (a) molding a calcium phosphate powder;
   (b) preliminarily calcining the resulting molding until closed pores are formed; and
   (c) firing said molding in air, an inert gas, or nitrogen gas, wherein said preliminary calcining is carried out under a pressure of less than 1 Torr and at a temperature of from 950° to 1,000° C.

2. A method for producing a calcium phosphate-based material as claimed in claim 1, wherein said preliminary calcinating is carried out in a vacuum or under a reduced pressure until the relative density is 95% or more.

3. A method for producing a calcium phosphate-based material as claimed in claim 1, wherein said final firing is carried out at a temperature of from 1,000° to 1,400° C.

4. A method for producing a calcium phosphate-based material as claimed in claim 2, wherein said calcium phosphate powder is at least one member selected from the group consisting of $Ca_{10}(PO_4)_6(OH)_2$, $Ca_3(PO_4)_2$, $Ca_2P_2O_7$, $Ca(PO_3)_2$, $Ca_{10}(PO_4)_6F_2$, and $Ca_{10}(PO_4)_6Cl_2$.

5. A method for producing a calcium phosphate-based material as claimed in claim 4, wherein said calcium phosphate powder is $Ca_{10}(PO_4)_6(OH)_2$.

6. A method for producing a calcium phosphate-based material as claimed in claim 1, wherein said preliminary calcinating is carried out from about 0.5 to 5 hours.

7. A method for producing a calcium phosphate-based material as claimed in claim 1, wherein said inert gas is argon gas or helium gas.

8. A method for producing a calcium phosphate-based material as claimed in claim 1, wherein said firing is carried out from about 0.5 to 5 hours.

* * * * *